United States Patent

Amano et al.

[11] Patent Number: 5,814,649
[45] Date of Patent: Sep. 29, 1998

[54] PREVENTIVE AND REMEDY FOR TYPE 1 ALLERGIC DISEASES

[75] Inventors: Yukio Amano, Hidaka; Yuko Mizushima, Tokyo; Kenji Ogata, Otawara, all of Japan

[73] Assignee: Hoechst Pharmaceuticals & Chemicals K.K., Tokyo, Japan

[21] Appl. No.: 817,241

[22] PCT Filed: Oct. 4, 1995

[86] PCT No.: PCT/JP95/02027

§ 371 Date: Jun. 6, 1997

§ 102(e) Date: Jun. 6, 1997

[87] PCT Pub. No.: WO96/11682

PCT Pub. Date: Apr. 25, 1996

[30] Foreign Application Priority Data

Oct. 17, 1994 [JP] Japan ................................. 6-250293

[51] Int. Cl.⁶ ........................... A61K 31/42; A61K 31/16
[52] U.S. Cl. ........................ 514/380; 514/378; 514/616; 514/625; 514/627
[58] Field of Search .................... 514/378, 380, 514/616, 625, 627

[56] References Cited

FOREIGN PATENT DOCUMENTS

B.10617959 10/1994 European Pat. Off. .
B.20529500 3/1995 European Pat. Off. .

*Primary Examiner*—Theodore J. Criares
*Attorney, Agent, or Firm*—Finnegan, Henderson, Farabow, Garrett & Dunner, L.L.P.

[57] ABSTRACT

A pharmaceutical composition for prophylaxis or treatment of Type I allergic diseases which comprises as an active ingredient an anilide compound represented by the general formula (I)

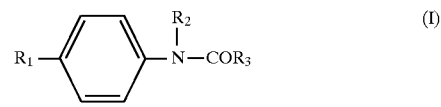

[wherein $R_1$ is a trifluoromethyl group, a halogen atom or a cyano group, $R_2$ is a hydrogen atom or a straight or branched $C_1$–$C_4$ alkyl group and $R_3$ is a group of the formula (II) or (III)

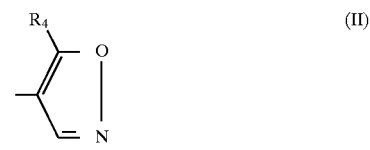

or

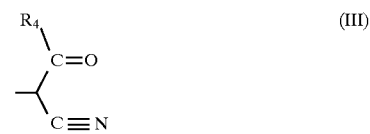

(wherein $R_4$ is a straight or branched $C_1$–$C_4$ alkyl group, a straight or branched $C_2$–$C_6$ alkenyl group, a straight or branched $C_2$–$C_6$ alkynyl group or a $C_2$–$C_6$ cycloalkyl group) or a stereoisomer thereof or a physiologically acceptable salt thereof.

The present composition remarkably inhibits the production of IgE, which is the direct cause of Type I allergic diseases, and it can radically prevent or cure Type I allergic diseases.

8 Claims, No Drawings

PREVENTIVE AND REMEDY FOR TYPE 1 ALLERGIC DISEASES

The present application has an effective international filing date of Oct. 4, 1995 as application Ser. No. PCT/JP95/02027 which designated the U.S. and entered the U.S. national phase on Apr. 14, 1997, under 35 USC 371, serial number not yet assigned.

FIELD OF THE INVENTION

This invention relates to a pharmaceutical composition for prophylaxis or treatment of Type I allergic diseases. More particularly, it relates to a pharmaceutical composition for prophylaxis or treatment of Type I allergic diseases which comprises as an active ingredient an anilide compound. Moreover, it relates to a use of an anilide compound for preparing a prophylactic or therapeutic agent for Type I allergic diseases. This invention is also concerned with a method for prophylaxis or treatment of Type I allergic diseases which comprises administering to a human being or a mammal an anilide compound.

BACKGROUND OF THE INVENTION

Allergic diseases are classified as Type I through Type IV. For their pathema, Type I may include pollinosis, asthma, atopic dermatitis and the like, Type II may include autoimmune hemolytic anemia, autoimmune thrombopenia and the like, Type III may include bacterial endocarditis, systemic lupus erythematosus and the like, Type IV may include tuberculosis, leishmaniasis, listeriosis and the like.

Mechanism of causing Type I allergic diseases is generally believed as discussed below. If allergens such as pollens, mites and the like are percutaneously or via the mucous membrane of respiratory organs or digestive organs introduced into the living body, immunoglobulin E (hereinafter referred to as IgE) is produced within the body to these allergens and such IgE is bound to basophilic leukocytes or mast cells via a receptor. If the allergen is taken again in the state where IgE is bound to basophilic leukocytes or mast cells via a receptor, that is, under a sensitized condition, the allergen may be bound to the sensitized basophilic leukocytes or mast cells, from which may be released chemical mediators such as histamine, leukotriene, serotonin and the like. These released substances may induce a contracting action of smooth muscles of the respiratory tract and blood vessel, a vasopermeability-accelerating action, an edematization action of the mucosa in the respiratory tract and a mucus secretion-accelerating action, and thus Type I allergic symptoms such as bronchial asthma, dermal inflammation and the like would be developed. ["Immunology Illustrated" (original, 2nd Ed.: translation-Supervised by Tomio Tada)]

As therapeutic agents for allergic diseases, there have been widely applied chemical mediator-release inhibitors such as Intal® (Fujisawa Pharmaceutical Co., Ltd.) (generic name: Disodium cromoglycate), chemical mediator-release inhibiting and antagonistic agents such as Celtect® (Kyowa Hakko Kogyo Co., Ltd.) (generic name: Oxatomide), Rizaben® (Kissei Pharmaceutical Co., Ltd.) (generic name: Tranilast) and synthetic adrenocortical hormones such as prednisolone. The mechanism of action of these drugs is that they inhibit the release of a chemical mediator capable of inducing allergic symptoms or they antagonize the chemical mediator thereby preventing the chemical mediator from binding to the corresponding receptor. Also, there may be utilized anti-inflammatory or immunosuppressive action of adrenocortical hormones. Problems involved in these drugs are that they are simply an agent usable for symptomatic treatment and should be taken whenever an allergen is introduced into the body to develop any symptoms, and that the allergic constitution itself which is characterized by a high blood IgE value is not treated at all.

DISCLOSURE OF THE INVENTION

It is an object of this invention to provide a pharmaceutical composition which can radically prevent or cure Type I allergic diseases by inhibiting the production of IgE which is the direct cause of Type I allergic diseases.

This invention is concerned with a pharmaceutical composition for prophylaxis or treatment of Type I allergic diseases which comprises as an active ingredient an anilide compound represented by the general formula (I)

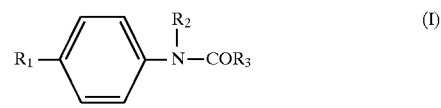

[wherein $R_1$ is a trifluoromethyl group, a halogen atom or a cyano group, $R_2$ is a hydrogen atom or a straight or branched $C_1C_4$ alkyl group and $R_3$ is a group of the formula (II) or (III)

or

(wherein $R_4$ is a straight or branched $C_1$–$C_4$ alkyl group, a straight or branched $C_2$–$C_6$ alkenyl group, a straight or branched $C_2$–$C_6$ alkynyl group or a $C3$–$C_6$ cycloalkyl group) or a stereoisomer thereof or a physiologically acceptable salt thereof.

This invention is further concerned with a method for prophylaxis or treatment of Type I allergic diseases which comprises administering to a human being or a mammal an anilide compound having the above formula (I) or a stereoisomer thereof or a physiologically acceptable salt thereof. Moreover, this invention is concerned with a use of an anilide compound of the above formula (I) or a stereoisomer thereof or a physiologically acceptable salt thereof for preparing a prophylactic or therapeutic agent for Type I allergic diseases.

In the definitions of $R_1$–$R_4$ in the above formula (I), a halogen atom may include, for example, fluorine, chlorine, bromine and iodine, and chlorine and bromine are particularly preferable. Straight or branched $C_1$–$C_4$ alkyl groups may include, for example, methyl, ethyl, n-propyl, isopropyl, n-butyl, isobutyl, t-butyl and other, and a straight or branched $C_1$–$C2$ alkyl group is preferable. Straight or branched $C_2$–C6 alkenyl groups may include, for example, vinyl, allyl, 2- or 3-butenyl, 1-methyl-3-butenyl, 3-, 4- or 5-pentenyl, 1-methyl -5-pentenyl, 3-, 4- or 6-hexenyl and others and a $C_2$–C4 alkenyl group is particularly preferable. Straight or branched C2–C6 alkynyl groups may include, for example, ethynyl, propargyl, 1-methyl-2-propynyl, 2- or 3-butynyl, 1-methyl2-butynyl, 3-, 4- or 6-hexynyl and others, and a $C_2$–C4 alkynyl group is particularly preferable. $C_3$–C7 cycloalkyl groups may include, for example, cyclopropyl, cyclobutyl, cyclopentyl, cyclohexyl, cycloheptyl and others, and a C3–C5 cycloalkyl group is preferable. Preferably, $R_1$ is trifluoromethyl, chlorine, bromine or cyano, $R_2$ is hydrogen, methyl or ethyl, $R_3$ is isoxazole or a group of the above formula (II) or (III), $R_4$ is methyl, ethyl, propyl, allyl, 2-butenyl, propargyl, 2-butynyl, cyclopropyl or cyclobutyl and others. Preferable examples of the compounds having the above formula (I) are 5-methylisoxazole-4-carboxylic acid-N-(4-trifluoromethyl) anilide (generic name: leflunomide), N-(4-trifluoromethylphenyl)-2-cyano-3-hydroxy-crotonamide (Compound A), 1-(3-methyl-4-trifluoromethylphenylcarbamoyl)-2-cyclopropyl-2-oxo-propionitrile (Compound B), 2-cyano-3-cyclopropyl-3-oxo-N-methyl-N-(4-chlorophenyl) -propionamide (Compound C), 2-cyano-3-cyclopropyl-3-oxo-(4-cyanophenyl) propionamide (Compound D), 2-cyano-3-oxo-N-[4-(trifluoromethyl)phenyl]-6-heptinamide (Compound E) and others.

Leflunomide is also known to be converted to pharmacologically active Compound A as defined above by rapid metabolism after administration.

Leflunomide has $LD_{50}$ (p.o.) values of 445 mg/kg in mice and 235 mg/kg in rats [Investigator's Brochure, Version 3: LEFULNOMIDE (HWA 486), October 1989, revised August 1991]. Previous studies using diseased animal models have revealed that leflunomide and the above-defined Compound A have an effect on autoimmune diseases such as articular rheumatism, systemic lupus erythematosus and the like [Japanese Patent Laid Open to Public No. Sho 62-72614, Bartlett, R. et al., "Springer Semin Immunopathol" (1993), 14:381–394]. And further, it is known that leflunomide has an inhibitory effect on histamine-release from mast cells [Bartlett, R. et al. "Spinger Semin Immunopathol", (1993) 14:381–394]. This could suggest that leflunomide possesses an inhibitory action on chemical mediator-release just like conventional therapeutic agents for allergic diseases.

The above-defined Compounds B–D are disclosed in Japanese Patent Laid Open to Public Application No. 288048/1993 and the above-defined Compound E is disclosed in EPA 551230, and they are known to have an anti-inflammatory action.

As a result of extensive studies by the present inventors, it has been elucidated that the anilide compounds of the above formula (I) can remarkably inhibit the production of IgE itself, which is the direct cause of Type I allergic diseases, upon which this invention has been completed.

More specifically, it has been found out that, when the above-defined anilide compound (I) is given to Brown Norway (BN) rats known to be a diseased animal model of Type I allergic diseases, it can remarkably inhibit the IgE production in BN rats and consequently exert a superior effect as a complete therapeutic agent for Type I allergic diseases. As discussed hereinabove, the known therapeutic agents for Type I allergic diseases have their main mechanism of action on the inhibition of the release of chemical mediators and they have no action to inhibit the IgE production itself.

Accordingly, it is a primary object of this invention to provide a new use of the above-defined anilide compound (I) as a prophylactic or therapeutic agent for Type I allergic diseases.

Another object of this invention is to provide a prophylactic or therapeutic composition for Type I allergic diseases which comprises as an active ingredient the above-defined anilide compound (I) in combination with a pharmaceutically acceptable carrier or diluent.

A still another object of this invention is to provide a method for prophylaxis or treatment of Type I allergic diseases which comprises administering to a human being or a mammal in need of said prophylaxis or treatment, as an active ingredient, an effective amount of the above-defined anilide compound (I).

These and other objects of this invention will be apparent from the following description of this invention.

Clinical daily dose for adults of the above-defined anilide compound (I) may vary depending upon the administration route and the age, body weight and symptoms of patients and others, and is usually in the range of 5–20 mg. Leflunomide has been applied to 500 or more cases abroad as a therapeutic agent for rheumatic arthritis and, the experience in those applications teaches that a usual dosage as defined above, i.e. 5–20 mg/patient/day could not cause the problems of side-effects, toxicity and the like.

For administration, there may be employed intravenous, intramuscular, oral, rectal and other routes and, in the case of intravenous administration, one may apply an intravenous drip injection besides usual intravenous injection.

A pharmaceutical preparation containing leflunomide may be prepared according to a conventional method using usual excipients, additives and the like.

Injectable preparations may include, for instance, a powdery preparation for injection. In that case, suitable water-soluble fillers, e.g. one or more of mannitol, sucrose, lactose, maltose, glucose, fructose and the like are added and the resultant mixture is dissolved in water. The solution is poured into vials or ampoules, freeze-dried and then sealed to form the preparation. In addition, it may be administered nasally or via lung in the form of a fine aerosol preparation for systemic administration.

Oral preparations may be in the forms of conventional tablets, capsules, granules, fine granules, powders, as well as enteric coated preparations.

In the case of enteric coated preparations, there may be added, as required, additives such as fillers, e.g. mannitol, sucrose, lactose, maltose, starch, silicic anhydride, calcium phosphate and the like, lubricants, e.g. talc, magnesium stearate and the like, binders, e.g. carboxymethylcellulose, methylcellulose, gelatine, acacia and the like, disintegrators, e.g. calcium carboxymethylcellulose and the like, thereby forming tablets, granules, fine granules and the like. And then, one or more of enteric coating bases such as cellulose acetate phthalate, hydroxypropylmethylcellulose phtalate, hydroxypropylmethylcellulose, acetyl succinate, polyvinyl alcohol phthalate, styrene, a maleic anhydride copolymer, a styrene-maleic acid copolymer, a methyl methacrylate-metacrylic acid copolymer, a methyl acrylate-methacrylic acid copolymer and the like and, where necessary, a coloring agent, e.g. titanium oxide and the like may be added and then coating is effected to form a preparation. And further, the enteric coated granules or fine granules thus prepared may be charged into capsules to form enteric coated capsules.

Also, the capsules as prepared according to a conventional method may be enteric-coated by coating with the above-mentioned enteric coating base and alternatively it may be also possible to prepare enteric coated capsules using the capsules formed with the above-mentioned enteric coating base alone or its mixture with gelatin.

For suppositories, lipophilic bases such as semi-synthetic bases having blended cacao butter, aliphatic acid triglycerides and the like with aliphatic acid monoglycerides or aliphatic acid diglycerides at various ratios or hydrophilic bases such as polyethylene glycol or glycerogelatin and the like after melting by heating are added, uniformly mixed and molded by placing the mixture into a mold to prepare suppositories.

This invention will be fully illustrated by way of the following examples, but this invention is not to be limited to these examples.

EXAMPLE 1

Study of effects of the anilide compound (I) on Type I allergic diseases caused by ovalbumin (OVA) in rats Using female BN/Crj rats of 7 weeks old, sensitization by OVA was carried out as described below.

10 mg/kg of OVA and 300 mg/kg of aluminum hydroxide (Alum) were intraperitoneally given (10 ml/kg) on the day (day 0) of administration. On day 3, 7 and 9 after the sensitization, blood samples were collected, the serum was separated and IgE concentration was determined. On day 10 after the sensitization, 60 mg/kg of OVA dissolved in physiological saline was given to the rats from the tail vein to cause anaphylactic shock. On the other hand, blood samples were collected at the jugular vein before and after the induction of the anaphylactic shock by OVA, and, after separation of the plasma, histamine level was determined.

The drug suspended in 1% carboxymethylcellulose (CMC) was repeatedly given orally once a day from day 0 to 9. The dose was 2 mg/kg or 10 mg/kg for each of the Compounds A–E and 2 mg/kg for prednisolone (generic name) as a control. All animals in each group were weighed in the morning once a week and the drug was given upon the body weights as weighed. To the solvent control group was given a 1% CMC solution. And further, non-medicated groups and non-treated groups were prepared. No treatment was applied to the non-treated group. The test was carried out using 6 rats per group.

The effect of the anilide compounds (I) on BN rats was evaluated from the survival rates of BN rats, the IgE levels in the sera and the histamine levels in the plasma before and after the induction of anaphylactic shock by OVA.

The results are shown in Table 1.

TABLE 1

Effect on OVA-sensitized rat anaphylactic models

| Sensitization | Added Compound | Dose (mg/kg) | No. of animal | Survival Rate (%) |
|---|---|---|---|---|
| — | — | — | 6 | 100 |
| OVA | 1% CMC | — | 5 | 0 |
| OVA | Leflunomide | 2 | 6 | 100 |
| OVA | Compound A | 10 | 3 | 33 |
| OVA | Compound B | 10 | 6 | 100 |
| OVA | Compound C | 10 | 6 | 100 |
| OVA | Compound D | 10 | 6 | 100 |
| OVA | Compound E | 10 | 5 | 100 |
| OVA | Prednisolone | 2 | 6 | 0 |

From the above results, it can be seen that in the OVA and 1% CMC-given groups and the OVA and prednisolone (2mg/kg)-given groups, all animals died from anaphylactic shock within 20 minutes to 2 hours after its development, whereas in the non-treated control groups, the OVA and Compounds B–E (10 mg/kg)-given groups and the OVA and leflunomide (2 mg/kg)-given groups, all animals survived without any anaphylactic shock.

The IgE level in sera was determined using the homemade sandwich-type ELISA system. The results are shown in Table 2.

TABLE 2

IgE Level of BN rat sera on day 9 after OVA sensitization

| Sensitization | Added Compound | Dose (mg/kg) | No. of animal | IgE amount (μg/ml ± SD) |
|---|---|---|---|---|
| — | — | — | 6 | 4.3 ± 2.4 |
| OVA | 1% CMC | — | 5 | 296.7 ± 96.0 |
| OVA | Leflunomide | 2 | 6 | 0.4 ± 0.1 |
| OVA | Compound A | 10 | 3 | 0.3 ± 0.0 |
| OVA | Compound B | 10 | 6 | 0.6 ± 0.5 |
| OVA | Compound C | 10 | 6 | 0.5 ± 0.1 |
| OVA | Compound D | 10 | 6 | 0.6 ± 0.1 |
| OVA | Compound E | 10 | 5 | 0.4 ± 0.1 |
| OVA | Prednisolone | 2 | 6 | 148.1 ± 72.0 |

SD: Standard deviation

From the above results, it can be seen that in the OVA and 1% CMC-given groups, extremely high level of 296.7 μg/ml was attained on day 9 after the sensitization, as compared with 4.7 μg/ml in the non-treated control groups. The serum IgE level in the prednisolone-given groups was increased up to 148.1 μg/ml. As compared with these groups, the serum IgE levels in the leflunomide-given groups were decreased conversely down to 0.4 μg/ml in the 2 mg/kg-given groups and 0.3–0.6 μg/ml in the Compounds A–E 10 mg/kg-given groups, respectively. From these results, it was found that the anilide compounds (I) could perfectly inhibit the increase in the serum IgE level at a dose of 2–10 mg/kg after the antigen sensitization.

Then, the plasma histamine levels before and after the induction of the anaphylactic shock by OVA on day 10 after OVA sensitization were determined as a parameter for allergic reactions. The results are shown in Table 3.

TABLE 3

Plasma histamine levels before and after the induction of the anaphylactic shock by OVA on day 10 after OVA administration

| Sensitization | Added Compound | Dose (mg/kg) | No. of animal | Histamine amount (μM ± SD) Before OVA challenge | After OVA challenge |
|---|---|---|---|---|---|
| — | — | — | 6 | 0.2 ± 0.1 | 0.1 ± 0.0 |
| OVA | 1% CMC | — | 5 | 0.3 ± 0.1 | 29.1 ± 9.2 |
| OVA | Leflunomide | 2 | 6 | 0.2 ± 0.1 | 0.1 ± 0.1 |
| OVA | Compound A | 10 | 3 | 0.2 ± 0.1 | 0.1 ± 0.0 |
| OVA | Compound B | 10 | 6 | 0.4 ± 0.1 | 1.3 ± 1.8 |
| OVA | Compound C | 10 | 6 | 0.3 ± 0.2 | 0.1 ± 0.0 |
| OVA | Compound D | 10 | 6 | 0.4 ± 0.2 | 0.6 ± 0.5 |
| OVA | Compound E | 10 | 5 | 0.3 ± 0.1 | 0.1 ± 0.0 |
| OVA | Prednisolone | 2 | 6 | 0.6 ± 0.4 | 23.6 ± 9.8 |

SD: Standard deviation

From the above results, it was observed after causing the shock that the plasma histamine level was noticeably increased in the OVA and 1% CMC-given groups and the prednisolone-given groups, whereas no increase in the plasma histamine level was observed in the non-treated control groups and the anilide compound (I)-given groups. It is known that histamine release is induced by binding an antigen with the IgE-sensitized basophilic leukocytes or mast cells. Accordingly, it is believed in this test that the IgE antibody specific to OVA was produced in a large amount by OVA administration, which might cause the anaphylactic shock by OVA and the histamine release at a high level in the OVA and 1% CMC-given groups and the prednisolone-given groups. Also, it is believed that the anilide compound (I) did completely inhibit the IgE production after OVA sensitization, which led to the complete inhibition of anaphylactic shock caused by OVA and histamine release at a high level.

EXAMPLE 2

Study on minimum effective dose of leflunomide

Using female BN/Crj rats of 7 weeks old, sensitization by OVA was carried out as described below. 10 mg/kg of OVA and 300 mg/kg of aluminum hydroxide (Alum) were intraperitoneally given on the day (day 0) of administration. Blood samples were collected on day 3, 5, 7 and 9 after the sensitization, the serum was separated and IgE concentration was determined. And, 60 mg/kg of the OVA dissolved in physiological saline was given to the rats from the tail vein to cause anaphylactic shock.

The drug suspended in 1% carboxymethylcellulose (CMC) was repeatedly given orally once a day from day 0 to 9. The leflunomide doses were 0.5, 1 and 2 mg/kg. All animals in each group were weighed in the morning once a week and the drug was given upon the body weights as weighed. A 1% CMC solution was given to the solvent control group. And further, non-treated group was prepared as control to which no treatment was applied. The test was carried out using 6 rats per group. The results are shown in Table 4.

TABLE 4

Effect of leflunomide on OVA-sensitized rat anaphylactic models

| Sensitization | Added Compound | Dose (mg/kg) | No. of animal | Survival Rate (%) |
|---|---|---|---|---|
| — | — | — | 6 | 100 |
| OVA | 1% CMC | — | 6 | 0 |
| OVA | Leflunomide | 0.5 | 5 | 0 |
| OVA | Leflunomide | 1 | 4 | 100 |
| OVA | Leflunomide | 2 | 6 | 100 |

From the above results, it can be seen that all animals died from anaphylactic shock within 20 minutes to 2 hours after the shock caused in the OVA and 1% CMC-given group, and the OVA and leflunomide (0.5 mg/kg)-given group, whereas all animals survived without any anaphylactic shock in the non-treated control group, the OVA and leflunomide (1 mg/kg)-given group and the OVA and leflunomide (2 mg/kg)-given group. The results are shown in Table 5.

TABLE 5

Serum IgE level of BN rats on day 9 after OVA administration

| Sensitization | Added Compound | Dose (mg/kg) | No. of animal | IgE amount (µg/ml ± SD) |
|---|---|---|---|---|
| — | — | — | 6 | 3.6 ± 1.4 |
| OVA | 1% CMC | — | 6 | 491.5 ± 184.3 |
| OVA | Leflunomide | 0.5 | 5 | 357.7 ± 119.0 |
| OVA | Leflunomide | 1 | 4 | 0.8 ± 0.1 |
| OVA | Leflunomide | 2 | 6 | 0.4 ± 0.1 |

SD: Standard deviation

From the above results, it can be seen that the serum IgE levels in the OVA and 1% CMC-given group and the OVA and leflunomide (0.5 mg/kg)-given group were as extremely high as 491.5 µg/ml and 357.7 µg/ml, respectively, on day 9 after the OVA sensitization, as compared with 3.6 µg/ml in the non-treated group. As compared with those groups, the serum IgE level in the OVA and leflunomide (1 mg/kg)-given group and the OVA and leflunomide (2 mg/kg)-given group were conversely decreased down to 0.8 µg/ml and 0.4 µg/ml. It is apparent from the above results that leflunomide can inhibit an increase in the serum IgE level after the antigen sensitization.

Preparation Example 1: Powders

| Name of Component | Formulated Amount |
|---|---|
| Leflunomide | 200 mg |
| Lactose | 700 mg |
| Corn starch | 100 mg |

Preparation: Leflunomide passed through a 60 mesh sieve was admixed with lactose passed through a 50-mesh sieve and corn starch passed through a 120-mesh sieve by means of a V-type mixer to form powders.

Preparation Example 2: Granules

| Name of Component | Formulated Amount |
|---|---|
| The above defined Compound B | 200 mg |
| Lactose | 684 mg |
| Corn starch | 100 mg |
| Hydroxypropyl cellulose | 18 mg |

Preparation: The above-defined Compound B passed through a 60-mesh sieve was admixed with lactose passed through a 50-mesh sieve and corn starch passed through a 120-mesh sieve by means of a V-type mixer and then an aqueous solution of hydroxypropyl cellulose was added. The mixture was blended by means of a twin-screw kneader and then granulated by means of an extrusion granulating machine. The product was dried at 60° C. and grain-controlled by means of a oscillator to form granulates sieved through a 12-mesh screen and left on a 60 mesh screen.

Preparation Example 3: Tablets

| Name of Component | Formulated Amount |
|---|---|
| The above-defined Compound C | 20 mg |
| Lactose | 41 mg |
| Corn starch | 30 mg |
| Carboxyethyl cellulose calcium | 8.5 mg |
| Methyl cellulose 25 cp | 1.5 mg |
| Magnesium stearate | 1.0 mg |

Preparation: The above-defined Compound C, lactose, corn starch and carboxymethyl cellulose calcium were admixed by means of a V-type mixer and the mixture was kneaded with an aqueous solution of methyl cellulose. The mixture was granulated by means of a granulating machine and dried at 60° C. The dried granules were admixed with magnesium stearate and then tableted by means of a tableting machine to form tablets.

INDUSTRIAL UTILIZATION

Administration of the anilide compounds (I) according to this invention can remarkably inhibit the production of IgE, which is the cause of Type I allergic diseases, and then eliminate the cause of type I allergic diseases to accomplish prophylaxis and treatment of Type I allergic diseases. Accordingly, the anilide compounds of this invention are useful as a prophylactic or therapeutic agent for Type I allergic diseases.

What is claimed is:

1. A method for prophylaxis or treatment of Type I allergic diseases which comprises administering to a human being or a mammal in need of said prophylaxis or treatment, an anilide compound represented by the general formula (I)

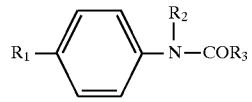
(I)

wherein $R_1$ is a trifluoromethyl group, a halogen atom or a cyano group, $R_2$ is a hydrogen atom or a straight or branched $C_1$–$C_4$ alkyl group and $R_3$ is a group of the formula (II) or (III)

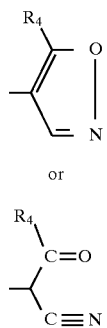

wherein $R_4$ is a straight or branched $C_1$–$C_4$ alkyl group, a straight or branched $C_2$–$C_6$ alkenyl group, a straight or branched $C_2$–$C_6$ alkynyl group or a $C_3$–$C_6$ cycloalkyl group or a stereoisomer thereof or a physiologically acceptable salt thereof.

2. A method for prophylaxis or treatment of Type I allergic diseases which comprises administering to a human being or a mammal in need of such treatment, an anilide compound represented by the general formula (I)

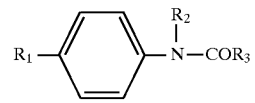

wherein, in said formula (I), $R_1$ is a trifluoromethyl group, a halogen atom or a cyano group, $R_2$ is a hydrogen atom or a straight or branched $C_1$–$C_4$ alkyl group, $R_3$ is a group of said formula (II) or (III), and $R_4$ is a straight or branched $C_1$–$C_2$ alkyl group, a straight or branched $C_2$–$C_4$ alkenyl group, a $C_2$–C4 alkynyl group or a $C_3$–$C_5$ cycloalkyl group.

3. A method according to claim 1 wherein the compound is 5-methylisoxazole-4-carboxylic acid-N-(4-trifluoromethyl)anilide.

4. A method according to claim 1 wherein the compound is N-(4-trifluoromethylphenyl)-2-cyano-3-hydroxy-crotonamide.

5. A method according to claim 1 wherein the compound is 1-(3-methyl-4-trifluoromethylphenylcarbamoyl)-2-cyclopropyl-2-oxo-propionitrile.

6. A method according to claim 1 wherein the compound is 2-cyano-3-cyclopropyl -3-oxo-N-methyl-N-(4-chlorophenyl)-propionamide.

7. A method according to claim 1 wherein the compound is 2-cyano-3-cyclopropyl -3-oxo-(4-cyanophenyl) propionamide.

8. A method according to claim 1 wherein the compound is 2-cyano-3-oxo-N-[4-(trifluoromethyl)phenyl]-6-heptinamide.

* * * * *

UNITED STATES PATENT AND TRADEMARK OFFICE
CERTIFICATE OF CORRECTION

PATENT NO. : 5,814,649
DATED : September 29, 1998
INVENTOR(S) : AMANO et al.

It is certified that error appears in the above-indentified patent and that said Letters Patent is hereby corrected as shown below:

Title Page, Item [57], in the Abstract,
    line 6, before "wherein", delete "[";
    line 13, before "wherein", delete "("; and
    line 15, after "group" (second occurrence), delete ")".

Claim 2, column 10, line 16, "$C_2$-C4" should read --$C_2$-$C_4$--.

Signed and Sealed this

First Day of June, 1999

Attest:

*Attesting Officer*

Q. TODD DICKINSON

*Acting Commissioner of Patents and Trademarks*